United States Patent [19]
Ogami

[11] 4,192,313
[45] Mar. 11, 1980

[54] FORCEPS DESIGNED TO FACILITATE INSERTION OF A LAMINARIA TENT INTO THE UTERINE CERVIX

[76] Inventor: Noboru Ogami, 34 Gartley Pl., Honolulu, Hi. 96817

[21] Appl. No.: 767,546

[22] Filed: Feb. 10, 1977

[51] Int. Cl.² .............................................. A61B 17/28
[52] U.S. Cl. .................... 128/321; 128/263; 128/341; 81/425 R
[58] Field of Search ............... 128/321, 322, 263, 285, 128/270, 127, 130, 131, 340, 354, 341; 81/425 R, 425 A; 29/268

[56] References Cited

U.S. PATENT DOCUMENTS

| | | | |
|---|---|---|---|
| 828,146 | 8/1906 | Somers | 128/324 |
| 1,910,750 | 5/1933 | Clark | 81/425 R |
| 2,583,892 | 1/1952 | Shellhouse | 128/321 |
| 2,618,268 | 11/1952 | English | 128/321 |
| 2,847,889 | 8/1958 | Cain | 81/425 R |
| 3,446,211 | 11/1967 | Markham | 128/322 |
| 3,631,707 | 1/1972 | Miller | 128/325 |
| 3,844,274 | 10/1974 | Nordstrom | 128/321 |
| 3,921,640 | 11/1975 | Freeborn | 128/321 |

FOREIGN PATENT DOCUMENTS

| | | | |
|---|---|---|---|
| 387740 | 7/1908 | France | 81/425 R |
| 4688 | of 1893 | United Kingdom | 128/321 |
| 149396 | 8/1920 | United Kingdom | 81/425 R |

*Primary Examiner*—Robert W. Michell
*Assistant Examiner*—Arthur S. Rose
*Attorney, Agent, or Firm*—Robert E. Geauque

[57] ABSTRACT

A forceps constructed of a pair of interconnected members in which the fore end of the pair of members each include a plurality of elongated grooves. The elongated grooves of the members are to cooperate together to facilitate clamping onto a Laminaria tent for insertion into the uterine cervix of a human female. In the longitudinal direction the grooves are inwardly tapered. The upstanding sidewalls separating the grooves assure a positive lock onto a variety of diameters of Laminaria tents.

2 Claims, 6 Drawing Figures

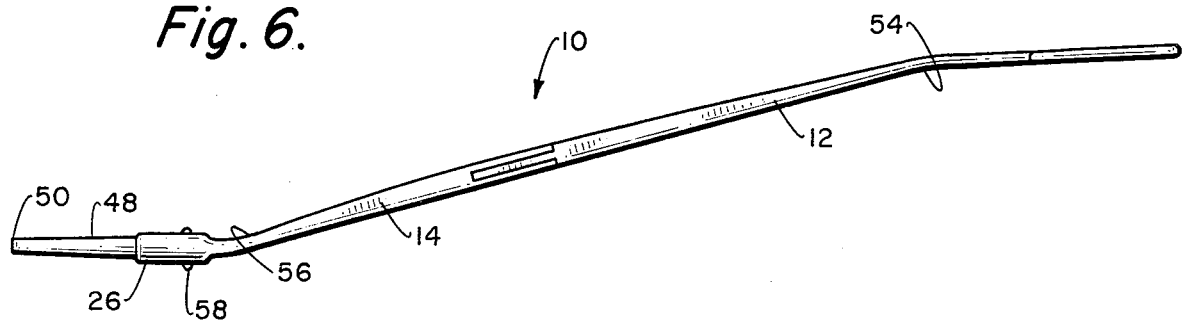

FORCEPS DESIGNED TO FACILITATE INSERTION OF A LAMINARIA TENT INTO THE UTERINE CERVIX

BACKGROUND OF THE INVENTION

The field of this invention relates to medical instruments and more particularly to a forceps to facilitate the insertion of a Laminaria tent to within the uterine cervix of the human female.

Within the past few years, the use of a Laminaria tent within the United States has become acceptable and widespread. The composition of the Laminaria tent is the root of a seaweed. The seaweed root is substantially dehydrated when used. The root, which is substantially the diameter of a pencil, is located within the opening of the uterine cervix. This root is remained in place for a period of several hours at which time the root absorbs moisture and swells. The swelling in size is substantial in comparison to the initial diameter of the root as the root will swell to three quarters of an inch to one inch in diameter. This swelling takes place slowly and therefore provides a means for gradual, safe and painless dilation of the uterine cervix in preparation for intrauterine procedures. An example of an intrauterine procedure would be an abortion. Through the use of the Laminaria tent, the necessity for the rapid physical stretching of the opening of the cervix is eliminated. Such rapid stretching frequently causing tearing of tissues.

Previously, there has been no known instruments specifically designed to be used to grasp and place the Laminaria tent within the cervical canal. Makeshift instruments have been used, such as the conventional ring sponge forceps or the Bozeman uterine dressing forceps. The disadvantage of using these instruments has been mainly the insecure grasp the instruments have on the Laminaria tent resulting in a lack of control in directing the Laminaria tent into the cervical canal. This is because the grasping surface of both the ring forceps and the Bozeman forceps is flat, while the Laminaria tent is a cylindrical object.

SUMMARY OF THE INVENTION

The forceps of this invention is comprised of a pair of members pivotally connected together intermediate their ends. The back end of each of the members include means to facilitate grasping and moving of the members in a scissor-like motion. The fore end of the members each include a plurality of longitudinally located elongated grooves. Each of the grooves are separated by a longitudinal ridge. This groove arrangement, as well as the ridges, facilitates secure grasping onto a variety of diameters of cylindrically-shaped Laminaria tents.

The objectives of the structure of the forceps of this invention is as follows:

1. To grasp the cylindrical Laminaria tent firmly. The concave inner surface of the grasping jaws of the forceps snugly accommodates the convex surface of the Laminaria tent.

2. To be able to grasp Laminaria tents of different diameters. The upstanding walls or ridges on the inner surface of the grasping jaws of the forceps is specifically designed to grasp firmly Laminaria tents of different diameters.

3. To facilitate alignment of a Laminaria tent to the axis of the cervical canal. The angulation of the longitudinal axis of the cervical canal and its relationship with the longitudinal axis of the vagina will vary depending upon the position of the body in the uterus, ie, the angle of the cervical canal versus the axis of the vagina may vary from an acute angle to an obtuse angle. The forceps is bent in two places along its longitudinal length so as to be able to direct the Laminaria tent more anteriorly as needed. The short length of the grasping jaws of the forceps also adds to the anterior direction of the Laminaria tent.

4. To insert the Laminaria tent to the desired depth. The wide, blunt tip of the forceps allows it to be placed against the external end of the Laminaria tent in order to push it into the desired depth.

BRIEF DESCRIPTION OF THE DRAWING

FIG. 6 is a side elevational view of the forceps of this invention taken along line 6—6 of FIG. 1.

DETAILED DESCRIPTION OF THE SHOWN EMBODIMENT

Figure 1:
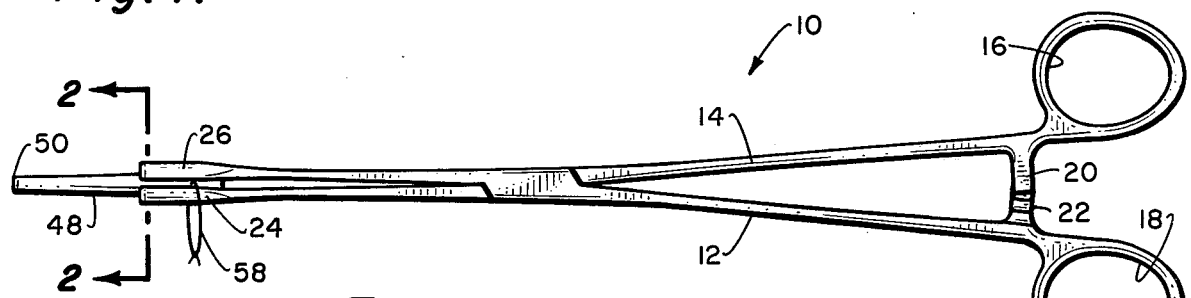
FIG. 1 is a plan view of the forceps of this invention showing such in a clamping position upon a Laminaria tent.

Referring particularly to the drawing, there is shown the forceps 10 of this invention which is constructed of a pair of members 12 and 14 which are pivotally interconnected together intermediate their links by a pivot pin assembly (not shown). Each of the members 12 and 14 are basically identical in length. The back end of the member 14 includes a thumb receiving opening 16. A finger receiving opening 18 is formed in the back end of the member 12. Adjacent the openings 16 and 18 is a locking means in the form of member 20, attached to member 14, and a member 22, attached to the member 12. Members 20 and 22 are to interconnect together and function to lock the forceps in the closed position. This type of locking arrangement is deemed to be conventional.

The fore end 24 of the member 14 is formed basically concave as is also the fore end 26 of the member 12. The concave inner surface of the ends 24 and 26 face each other so that essentially the ends 24 and 26 are basically mirror images of one another. The end 24 includes an enlarged centrally located longitudinal groove 28. A similarly centrally enlarged longitudinal groove 30 is formed on the inner surface of the end 26. Located on each side of the groove 28 are longitudinal side grooves 32 and 34. Similar side grooves 36 and 38 are located on each side of the groove 30. Each of the grooves are of identical length, such as about one inch.

Separating the grooves 28 and 34 is an upstanding sidewall or ridge 40. A similar upstanding sidewall or ridge 42 separates the grooves 28 and 32. A similar upstanding sidewall 44 separates the grooves 38 and 30. And also a similar upstanding sidewall 46 separates the grooves 30 and 36. Each of the sidewalls 40, 42, 44 and 46 extend the substantial longitudinal length of the grooves. Also, the outermost surface of each of the sidewalls is formed planar.

The forceps 10 of this invention is shown attached to a Laminaria test 48. The Laminaria tent 48 is to be formed of a seaweed root and is basically cylindrical in shape but is slightly tapered so that it outermost end 50 is of a smaller diameter than its innermost end 52. In order to accommodate this slight longitudinal tapering of the tent 48, each of the grooves within each of the ends 24 and 26 are also inwardly tapered, as is also the upstanding sidewalls located between the grooves. This arrangement insures that the clamping action of the fore ends 24 and 26 is snug against the exterior surface of the Laminaria tent 48.

Figure 2:
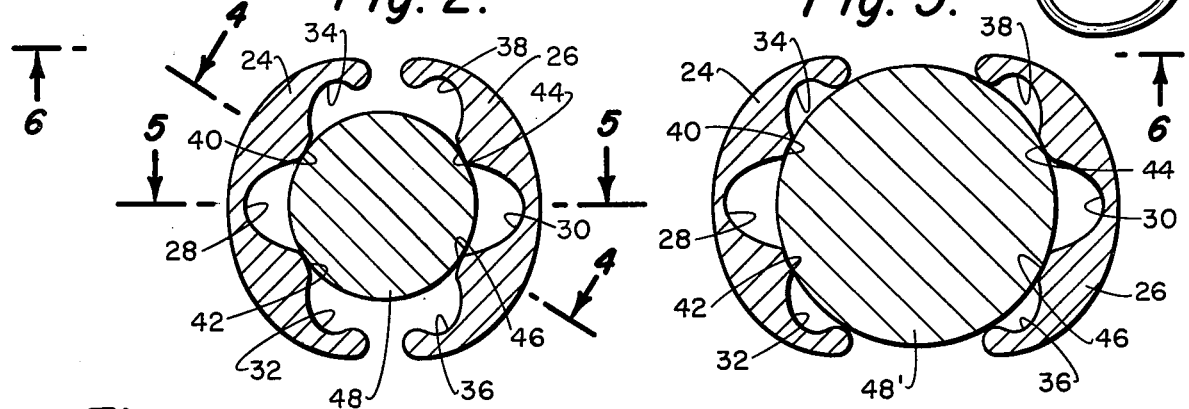
FIG. 2 is a cross-sectional view through the grasping end of the forceps taken along line 2—2 of FIG. 1.

Referring particularly to FIG. 2 of the drawing, a first size of Laminaria tent 48 is shown. This particular size happens to be a smaller diametered Laminaria tent (3 to 4 millimeters) and when a smaller diameter Laminaria tent is grasped by the forceps 10, the sidewalls 40, 42, 44 and 46 directly contact and are actually the only contact points upon the outer surface of the Laminaria tent 48. Actually, the Laminaria tent 48 is substantially smaller in size than the opening provided between the ends 24 and 26. Even so, because of the employing of the plurality of longitudinal grooves within each of the ends 24 and 26, the Laminaria tent 48 is centered within the opening between the ends 24 and 26 and is securely grasped by the edges of the upstanding sidewalls 40, 42, 44 and 46. The fully swollen tent 48 will be six to eight millimeters in diameter.

Figure 3:
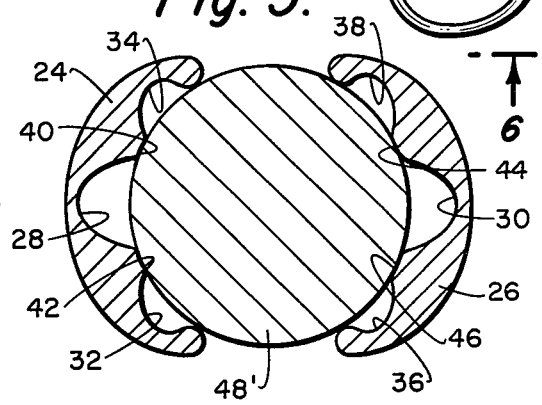
FIG. 3 is a view similar to FIG. 2 but showing the grasping end of the forceps in contact with a larger diametered Laminaria tent.
Figure 4:
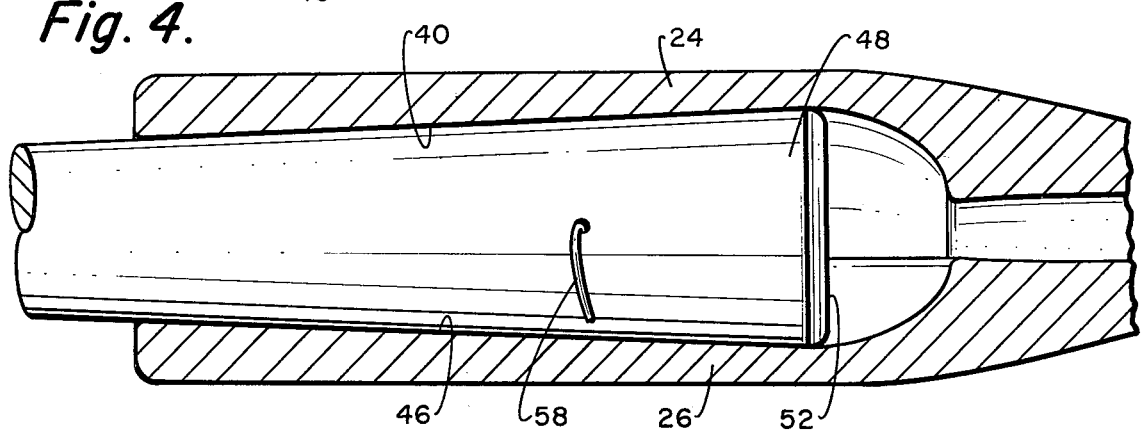
FIG. 4 is a cross-sectional view through the grasping end of the forceps of this invention taken along line 4—4 of FIG. 2.
Figure 5:
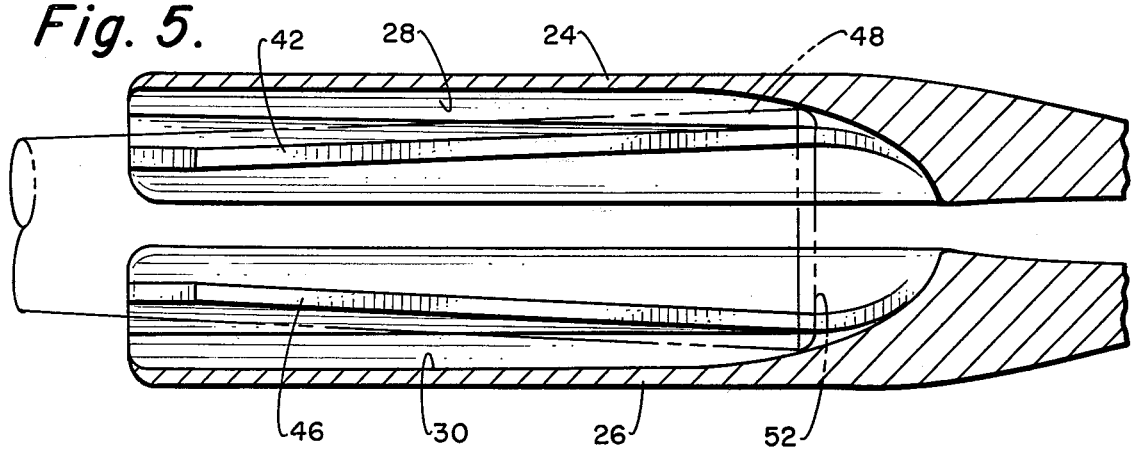
FIG. 5 is a cross-sectional view through the grasping end of the forceps of this invention taken along line 5—5 of FIG. 2.

Referring particularly to FIG. 3 of the drawings, there is shown a substantially larger diametered Laminaria tent 48' (6 to 7 millimeters). Actually, the forceps 10 of this invention could accommodate a larger size Laminaria tent, if desired. The size of tent 48' is such that not only are the upstanding sidewalls 40, 42, 44 and 46 contacting the outer surface of the tent 48', also the peripheral edges of the ends 24 and 26 are in contact with the exterior surface of the tent 48'. In any event, the Laminaria tent 48' is centered within the opening between the ends 24 and 26 and is securely grasped by the ends 24 and 26. The fully swollen tent 48' will be 1.2 to 1.4 centimeters.

At times, more than a single tent will be inserted in the cervix. If two or three of the larger tents 48' are inserted in a group, dilation of the cervix exceeding one inch can be obtained. Also, another desirable feature by use of such tents is that the cervical tissue becomes soft and easily dilatable.

In operation of the forceps 10 of this invention, it is to be understood that the Laminaria tent 48 or 48' is centrally located between the members 24 and 26 and then the members 12 and 14 move toward each other until locking arrangement provided by the members 20 and 22 firmly holds the forceps 10 in the locked position tightly grasping the Laminaria tent. The physician then inserts the Laminaria tent in its desired position within the uterine cervix of the patient. The physician then moves the members 12 and 14 to unlock the lock members 20 and 22 thereby releasing the hold upon the Laminaria tent 48 and the physician thereupon removes the forceps 10. In order to facilitate this inserting movement, it has been found to be desirable to construct the forceps 10 to include a first bend 54 and a second bend 56. As previously mentioned, these bends are merely for the purpose of facilitating the insertion of the Laminaria tent within the cervix.

The Laminaria tent will normally include a string 58 attached thereto adjacent the end 52. The purpose of the string 58 is to facilitate removal of the Laminaria tent 48 after dilation of the cervix has occurred. Upon the Laminaria tent having been removed, the physician is then free to perform the desired intrauterine operation.

What is claimed is:

1. A forceps for the insertion of a Laminaria tent into the uterine cervix comprising:

a first member;

a second member, said first and second members being pivotally connected together forming a scissors assembly, said first and second members being substantially of the same length, each said member having a fore end and an aft end, manual grasping means formed on the said aft end of said members, said fore end of said members including first means for clamping onto a Laminaria tent, said first means comprising:

said fore end of said first member being recessed into a first recess assembly;

said fore end of said second member being recessed into a second recess assembly, said first and second recess assemblies cooperating to clamp onto a Laminaria tent, the cross-sectional configuration of said first recess assembly being a mirror image of said second recess assembly, each said recess assembly including a plurality of side-by-side elongated grooves separated by elongated upstanding walls, the longitudinal dimensions of each said groove being substantially along the longitudinal dimension of its respective said first or second member, whereby the forceps may be universally used to clamp onto different diameters of Laminaria tents and thereby facilitate insertion of the Laminaria tent into the desired position within the uterine cervix; and each said recess assembly including a single enlarged elongated groove centered in accordance with the width dimension of its respective said fore end, each said recess assembly further including a single elongated side groove located on each side of said enlarged groove, said enlarged groove being of a larger size than said side grooves, said upstanding side walls of said enlarged elongated groove to be in physical contact with the smaller diametered Laminaria tent.

2. A forceps for the insertion of a Laminaria tent into the uterine cervix comprising:

a first member;

a second member, said first and second members being pivotally connected together forming a scissors assembly, said first and second members being substantially of the same length, each said member having a fore end and an aft end, manual grasping means formed on the said aft end of said members, said fore end of said members including first means for clamping onto a Laminaria tent, said first means comprising:

said fore end of said first member being recessed into a first recess assembly;

said fore end of said second member being recessed into a second recess assembly, said first and second recess assemblies cooperating to clamp onto a Laminaria tent, the cross-sectional configuration of said first recess assembly being a mirror image of said second recess assembly, each said recess assembly including a plurality of elongated grooves separated by elongated upstanding walls, whereby the forceps may be universally used to clamp onto different diameters of Laminaria tents and thereby facilitate insertion of the Laminaria tent into the desired position within the uterine cervix;

each said recess assembly being longitudinally lineally tapered with respect to its respective said first and second members so that the portion of said cooperating recess assemblies nearest said aft end forms a larger opening than the outer end of said cooperating recess assemblies; and each of said recess assembly including a single enlarged elongated groove centered in accordance with the width dimension of its respective said fore end, each said recess assembly further including a single elongated side groove located on each side of said enlarged groove, said enlarged groove being of a larger size than said side grooves, said upstanding side walls of said enlarged elongated groove to be in physical contact with the smaller diameter Laminaria tent.

* * * * *